(12) United States Patent
Ohtsuka

(10) Patent No.: US 6,404,985 B1
(45) Date of Patent: Jun. 11, 2002

(54) FUNDUS CAMERA FOR DIAGNOSTIC FUNDUS PHOTOGRAPHING

(75) Inventor: Hiroyuki Ohtsuka, Tokyo (JP)

(73) Assignee: Kabushiki Kaisha TOPCON, Tokyo (JP)

( * ) Notice: Subject to any disclaimer, the term of this patent is extended or adjusted under 35 U.S.C. 154(b) by 0 days.

(21) Appl. No.: 09/542,911

(22) Filed: Apr. 4, 2000

(30) Foreign Application Priority Data

Apr. 5, 1999 (JP) .......................................... 11-097214

(51) Int. Cl.$^7$ ............................. A61B 3/14; G03B 29/00
(52) U.S. Cl. ......................................... 396/18; 351/208
(58) Field of Search ..................... 396/18; 351/206–208

(56) References Cited

U.S. PATENT DOCUMENTS

| | | | | |
|---|---|---|---|---|
| 5,548,354 A | * | 8/1996 | Kasahara et al. | 396/18 |
| 5,572,266 A | * | 11/1996 | Ohtsuka | 396/18 |
| 5,594,512 A | * | 1/1997 | Yoneda et al. | 396/18 |
| 5,757,461 A | * | 5/1998 | Kasahara et al. | 396/18 |

* cited by examiner

*Primary Examiner*—David M. Gray
(74) *Attorney, Agent, or Firm*—Oblon, Spivak, McClelland, Maier & Neustadt, P.C.

(57) ABSTRACT

A fundus camera includes a main unit equipped with an illuminating optical system for illuminating the fundus of an eye to be inspected and a photographing optical system for photographing the fundus, an observation optical system for determining whether or not the distance between the main unit and the eye is equal to a proper working distance, an alignment index projecting system, and a driving mechanism for moving a light guide along an optical axis to change a working distance in the case of photographing the central part of the fundus and in the case of photographing a peripheral part of the fundus.

4 Claims, 9 Drawing Sheets

FUNDUS CAMERA FOR DIAGNOSTIC FUNDUS PHOTOGRAPHING

BACKGROUND OF THE INVENTION

1. Field of the Invention

The present invention relates to a fundus camera for diagnostic photographing of a fundus.

2. Description of the Related Art

A fundus camera photographs a peripheral part of a fundus as well as a central part of the fundus. When photographing a central part of the fundus, a fixation mark is projected along the optical axis of a photographing optical system on an eye to be inspected to align the visual line of the eye with the optical axis of the photographing optical system, and then the fundus of the eye is photographed. When photographing a peripheral part of the fundus, a fixation mark is projected in a direction different from the optical axis of the photographing system on the eye to direct the visual line of the eye in a direction different from the optical axis of the photographing system, and then the peripheral part of the fundus is photographed.

When photographing a peripheral part of the fundus by a conventional fundus camera, illuminating light projected by an illuminating optical system is reflected on the cornea and enters a photographing optical system, deteriorating the quality of a photograph. This problem will be explained with reference to FIGS. 12(a) and 12(b).

An illuminating optical system of a conventional fundus camera is provided with a cornea diaphragm (shading member) 1, an iris diaphragm 2, a lens diaphragm 3 and an objective 5. The cornea diaphragm 1, the iris diaphragm 2 and the lens diaphragm 3 prevents light rays from being reflected on the cornea, the iris and the back surface of the lens of an eye E to be inspected from entering a photographing optical system.

As shown in FIG. 12(a), when photographing a central part of the fundus Ef of the eye E, light rays passing an edge of the cornea diaphragm 1 are reflected by an aperture mirror (not shown), travel through the objective 5, fall on the eye E and are reflected by the cornea C in a direction diverting from a direction toward the objective 5. When the direction of the visual line of the eye E is changed to photograph a peripheral part of the fundus Ef, the aforementioned illuminating light rays are reflected by the cornea C toward the objective 5 as shown in FIG. 12(b), travel through the aperture of the aperture mirror, and enters a photographing optical system deteriorating the picture quality of photographs.

SUMMARY OF THE INVENTION

An object of the present invention is to provide a fundus camera capable of preventing the entrance of light rays reflected on the cornea in a photographing optical system when photographing a peripheral part of the fundus of an eye to be inspected, thereby providing a photographed image of an improved picture quality.

With the foregoing object in view, according to a first aspect of the present invention, there is provided a fundus camera comprising a main unit equipped with an illuminating system for illuminating the fundus of an eye to be inspected and a photographing system for photographing the fundus; a working distance detecting means for detecting whether a distance between the eye and the main unit is equal to a proper working distance or not; and a working distance changing means for changing the proper working distance depending on whether photographed part is a central part of the fundus or a peripheral part.

Even when photographing a peripheral part of the fundus, light reflected on the cornea does not enter the photographing system and, consequently, an image of an improved picture quality can be obtained.

According to a second aspect of the present invention, there is provided a fundus camera comprising an illuminating system for illuminating the fundus of an eye to be inspected, a photographing system for photographing the fundus, and shading members for preventing the entrance of illuminating light reflected on the cornea of the eye into the photographing system, the shape or the size of the shading members being changed depending on whether photographed part is a central part of the fundus or a peripheral part.

The effect of the fundus camera in the second aspect of the present invention is the same as that of the fundus camera in the first aspect of the present invention.

BRIEF DESCRIPTION OF THE DRAWINGS

The above and other objects, features and advantages of the present invention will become more apparent from the following description of the presently preferred exemplary embodiments of the invention taken in conjunction with the accompanying drawings, in which:

FIGS. 3(a) and 3(B) are diagrammatic views of assistance in explaining the principle of projecting an alignment index by the fundus camera in the first embodiment, in which FIG. 3(a) shows a state where an alignment image is formed on a plane conjugate with the fundus and is on the optical axis of a photographing optical system when the optical axis of the eye is aligned with the optical axis of the photographing optical system, and FIG. 3(b) shows a state where an alignment image is formed on a plane conjugate with the fundus but is displaced from the optical axis of a photographing optical system when the optical axis of the photographing optical system is inclined at a predetermined angle to the optical axis of the eye;

FIGS. 5(a) and 5(b) are pictorial views of fundus images observed by means of the fundus camera shown in FIG. 1, in which FIG. 5(a) shows the fundus image formed when a main unit of the fundus camera is at a proper working distance from the eye and FIG. 5(b) shows the fundus image formed when the main unit is at a distance not equal to the proper working distance from the eye;

FIGS. 6(a) and 6(b) are pictorial views of fundus images observed by means of the fundus camera shown in FIG. 1, in which FIG. 6(a) shows an image of a central part of the fundus displayed on a television monitor and an alignment image and FIG. 6(b) shows an image of a peripheral part of the fundus and an alignment image;

FIGS. 9(a) and 9(b) are diagrammatic views of assistance in explaining the principle of projecting an alignment index by a fundus camera in a second embodiment according to the present invention, in which FIG. 9(a) shows a state where an alignment image is formed on a plane conjugate with the fundus and is on the optical axis of a photographing optical axis system when the optical axis of the eye is aligned with the optical axis of the photographing optical system, and FIG. 9(b) shows a state where an alignment image is formed on a plane conjugate with the fundus but is on the optical axis of a photographing optical system the optical axis of the photographing optical system is inclined at a predetermined angle to the optical axis of the eye;

FIGS. 10(a) and 10(b) are front elevations of cornea diaphragms employed in a fundus camera in a third embodiment according to the present invention, in which FIG. 10(a) shows a cornea diaphragm used for photographing a central part of the fundus and FIG. 10(b) shows a cornea diaphragm used for photographing a peripheral part of the fundus;

FIGS. 11(a) and 11(b) are front elevations of other cornea diaphragms used in the fundus camera in the third embodiment, in which FIG. 11(a) shows a cornea diaphragm used for photographing a central part of the fundus and FIG. 11(b) shows a cornea diaphragm used for photographing a peripheral part of the fundus; and FIGS. 12(a) and 12(b) are diagrammatic views of an illuminating optical system of a conventional fundus camera, in which FIG. 12(a) shows a mode of photographing a central part of the fundus and FIG. 12(b) shows a mode of photographing a peripheral part of the fundus.

DESCRIPTION OF THE PREFERRED EMBODIMENTS

Preferred embodiments of the present invention will be described with reference to the accompanying drawings.

First Embodiment

Figure 1:
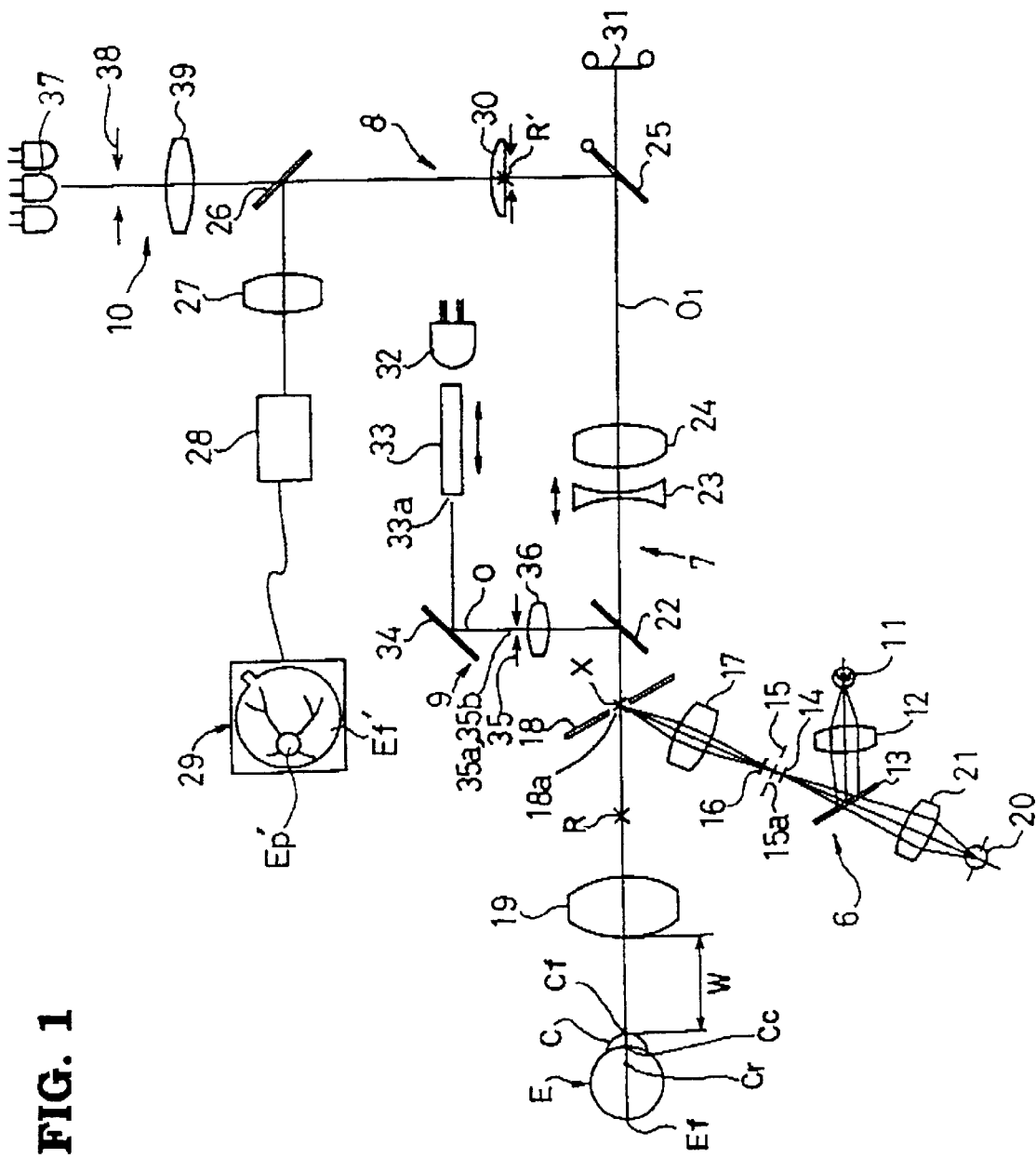
FIG. 1 is a diagrammatic view of a fundus camera in a first embodiment according to the present invention.

FIG. 1 shows an optical system of a fundus camera in a first embodiment according to the present invention. The fundus camera has an illuminating optical system 6, a photographing optical system 7, an observation optical system 8, an alignment index projecting optical system 9 and a fixation mark projecting optical system 10.

The illuminating optical system 6 includes an observation light source 11, a condenser lens 12, a dichroic mirror 13, a cornea diaphragm 14, an iris diaphragm 15, a lens diaphragm 16, a relay lens 17, an aperture mirror 18 and an objective 19. The dichroic mirror 13 transmits visible light rays and reflects infrared rays. The iris diaphragm 15 is provided with a ring-shaped opening 15a. The aperture mirror 18 is provided with an aperture 18a.

Illuminating light emitted by the observation light source 11 travels through the condenser lens 12, the dichroic mirror 13, the cornea diaphragm 14, the iris diaphragm 15, the lens diaphragm 16 and the relay lens 17 and is focused on a plane near the aperture mirror 18. The illuminating light is converted by the annular slit 15a of the iris diaphragm 15 into an annular-slit illuminating light. The illuminating optical system 6 is provided with a photographing light source 20 and a condenser lens 21 disposed behind the dichroic mirror 13.

When a photographing button (not shown), is depressed to photograph the eye E, the photographing light source 20 emits photographing light. The photographing light emitted by the photographing light source 20 travels through the condenser lens 21 and the dichroic mirror 13 and is focused on a plane near the aperture mirror 18, as is similar to the illuminating light emitted from the observation light source 11.

The photographing optical system 7 includes the objective 19, the aperture mirror 18, a semitransparent mirror 22 that reflects alignment light, a focusing lens 23, an image forming lens 24 and a lift mirror 25. The observation optical system 8 includes the lift mirror 25, a dichroic mirror 26 and a television relay lens 27. The observation optical system 8 constitutes an observation system together with a camera tube 28 and a television monitor 29.

Figure 2:
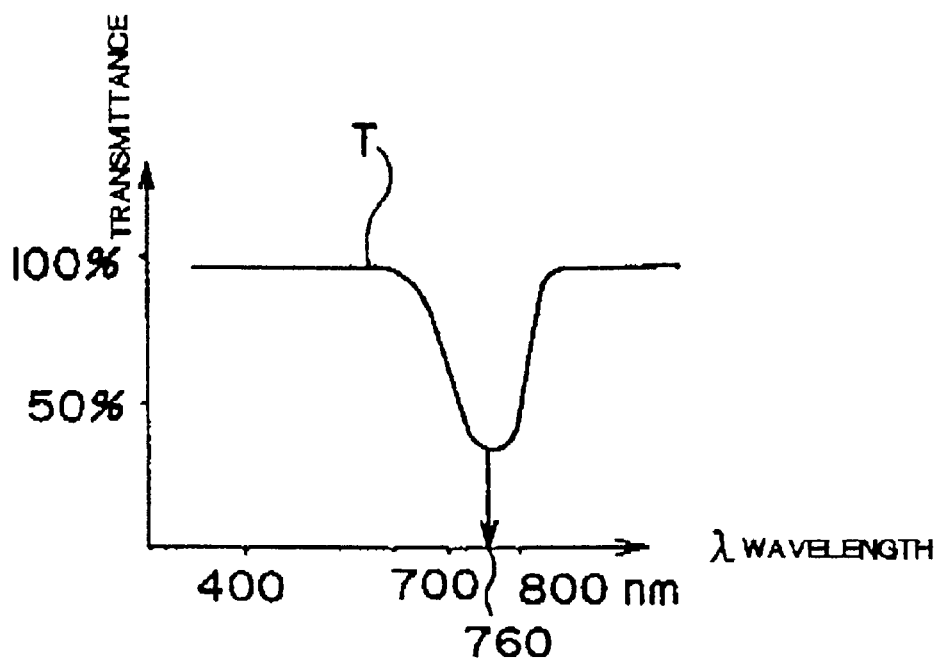
FIG. 2 is a graph showing the transmission characteristic of a semitransparent mirror included in the fundus camera shown in FIG. 1.

Reflected light from the fundus Ef of the eye E is guided by the objective 19 and is focused on a fundus conjugate plate R conjugate with the fundus Ef with respect to the objective 19. The reflected light travels through the aperture 18a of the aperture mirror 18, the semitransparent mirror 22, the focusing lens 23 and the image forming lens 24 and falls on the lift mirror 25. As shown in FIG. 2, the semitransparent mirror 22 has a transmission characteristic T to transmit about 30% of light rays of 760 nm in wavelength and about 100% of light rays of wavelengths other than 760 nm. Subsequently, the semitransparent mirror 22 does not reduce the intensity of reflected light reflected from the fundus Ef.

The reflected light is reflected by the lift mirror 25 to form a fundus image on a plane at a position R' where a field lens 30 is disposed. The focused reflected light travels through the dichroic mirror 26 and the television relay lens 27 and falls on the camera tube 28. A fundus image Ef' is displayed on the screen of the television monitor 29.

In the photographing optical system 7, a film 31 is disposed at a position conjugate with the field lens 30 with respect to the lift mirror 25. When photographing the fundus Ef, the lift mirror 25 is lifted away from the optical path of the photographing optical system 7 simultaneously with the actuation of the photographing light source 20 for light emission and the fundus, thereby Ef' being formed and recorded on the film 31.

The alignment index projecting optical system 9 includes a LED 32, i.e., an alignment light source, a light guide 33, a reflecting mirror 34, a two-aperture diaphragm 35, a relay lens 36 and the semitransparent mirror 22. The LED 32 emits near-infrared rays of 760 nm in center wavelength. An exit end (alignment index) 33a of the light guide 33 is located on the optical axis O of the relay lens 36, i.e., the optical axis $O_1$ of the photographing optical system 7.

Figure 3A:
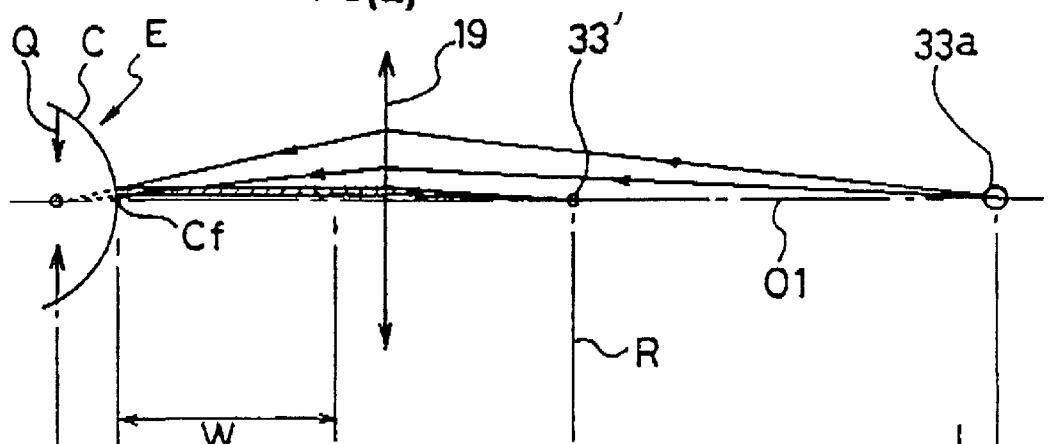
Figure 3B:
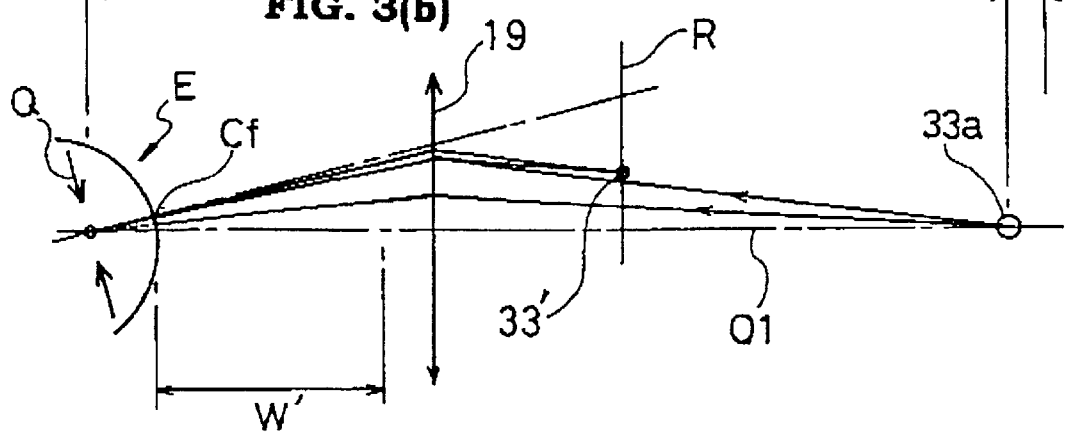

As shown in FIGS. 3(a) and 3(b), the light guide 33 is moved by a predetermined distance δ toward the eye E when the LED 32 for projecting a fixation mark for photographing a peripheral part of the fundus Ef is turned on. Consequently, the working distance W' of the fundus camera in case of photographing a peripheral part of the fundus is longer than the working distance W in case of photographing a central part of the fundus (proper working distance) (W<W'), and the light reflected from the cornea is prevented from entering the photographing optical system 7 and from reaching the film 31, which will be described later.

Figure 4A:
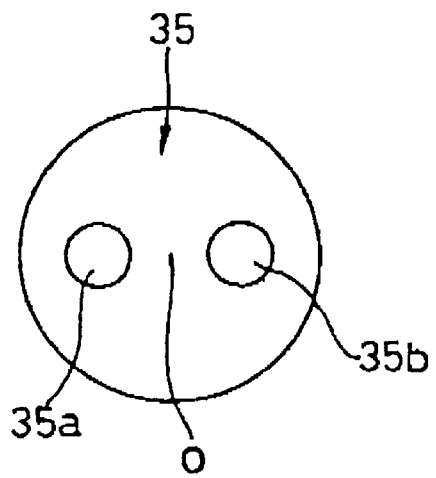
FIG. 4(a) is a front elevation of a two-hole diaphragm included in the first embodiment shown in FIG. 1.

The two-aperture diaphragm 35 is disposed close to the relay lens 36 between the reflecting mirror 34 and the relay lens 36. As shown in FIG. 4(a), the two-aperture diaphragm 35 is provided with a pair of apertures 35a and 35b arranged symmetrically with respect to the optical axis O. The relay lens 36 forms an image of the exit end 33a of the light guide 33 at the center X of the aperture 18a of the aperture mirror 18 on the optical axis $O_1$ of the photographing optical system 7.

Alignment light rays projected from the exit end 33a of the light guide 33 are reflected by the reflecting mirror 34 toward the apertures 35a and 35b of the two-aperture diaphragm 35. The alignment light rays travel through the apertures 35a and 35b and the relay lens 36 and are reflected by the semitransparent mirror 22 toward the aperture mirror 18.

A pair of alignment light beams reflected to the center X of the aperture 18a of the aperture mirror 18 travel through the objective 19 and fall on the cornea C of the eye E. When the main unit is located properly with respect to up-and-down and left-and-right directions with respect to the eye E (XY alignment) and the main unit is at the proper working distance W from eye E, the pair of alignment light beams form alignment images at a middle position Cc between the vertex Cf of the cornea C and the center Cr of curvature of the cornea C. When the main unit is dislocated from a proper position at the proper working distance W from the eye E, the pair of alignment beams form separate alignment images at the middle position Cc with the optical axis therebetween.

Figure 5A:
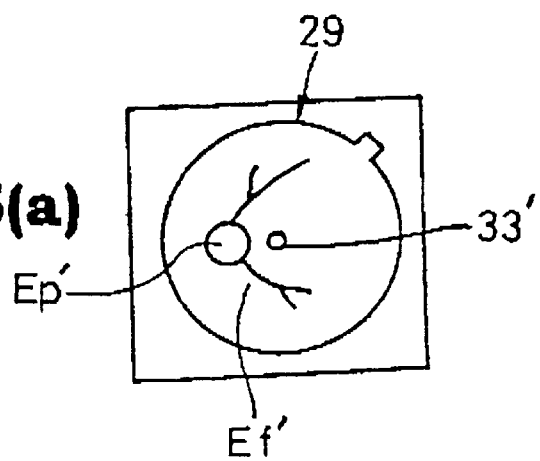

Reflected alignment light beams reflected from the cornea C are focused on a fundus-conjugate plane R conjugate with the fundus Ef by the objective 19 when the main unit is at the proper working distance W from the eye E. The reflected alignment light beams focused on the fundus-conjugate plane R travel through the aperture 18a of the aperture mirror 18 and fall, in a manner similar to the reflected light forming the fundus image Ef, on the camera tube 28. Consequently, alignment index images 33', i.e., images of the exit end 33a, are formed at the same position together with the fundus image Ef' on the screen of the television monitor 29 as shown in FIG. 5(a).

Figure 5B:
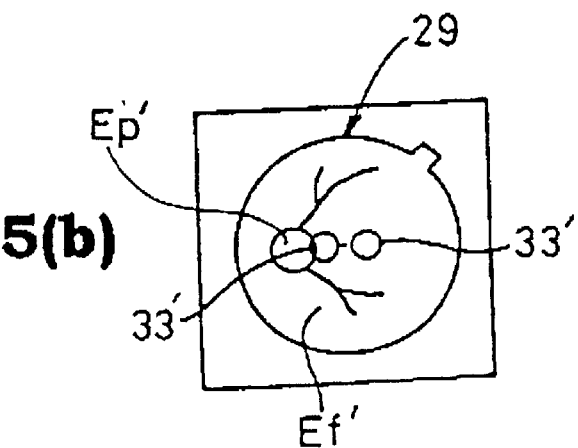

When the main unit is dislocated from a proper position at the proper working distance W from the eye E, the alignment index images 33' are displayed separately as shown in FIG. 5(b) on the screen of the television monitor 29. An inspector recognizes visually the coincidence or the separation of the alignment index images 33' formed by the alignment light beams, which will be described later. Patents relating to the present technique are issued as JP-B Nos. Sho 60-52820, Sho 60-57854, Sho 63-22823, Sho 60-57885 and Hei 5-54777 and JP-A No. Hei 6-277183.

The fixation mark projecting optical system 10 is disposed behind the dichroic mirror 26. The fixation mark projecting optical system 10 includes a plurality of fixation light sources 37, for example five fixation light sources 37, for guiding the visual line of the eye E, a diaphragm 38 serving as a fixation mark, and a fixation mark projection lens 39. A fixation light beam representing the fixation mark travels through the optical elements of the photographing optical system 7 and falls on the fundus Ef of the eye E. One of the five fixation light sources 37 is used when photographing a central part of the fundus Ef and the other four fixation light sources 37 are used when photographing a peripheral part of the fundus Ef. In FIG. 1, one fixation light source 37 for central part photographing and two fixation light sources 37 for peripheral part photographing are shown. The other two fixation light sources 37 for peripheral part photographing, are not shown in the drawing because they are put in a direction perpendicular to the paper of the drawing. When photographing a central part of the fundus Ef, the fixation light source 37 for central part photographing is turned on to project a fixation mark on the eye E. When photographing a peripheral part of the fundus Ef, such as a right part, a left part, an upper part or a lower part, the fixation light source 37 corresponding to the desired peripheral part of the fundus Ef (photographing part) is used to project a fixation mark on the eye E.

Figure 6A:
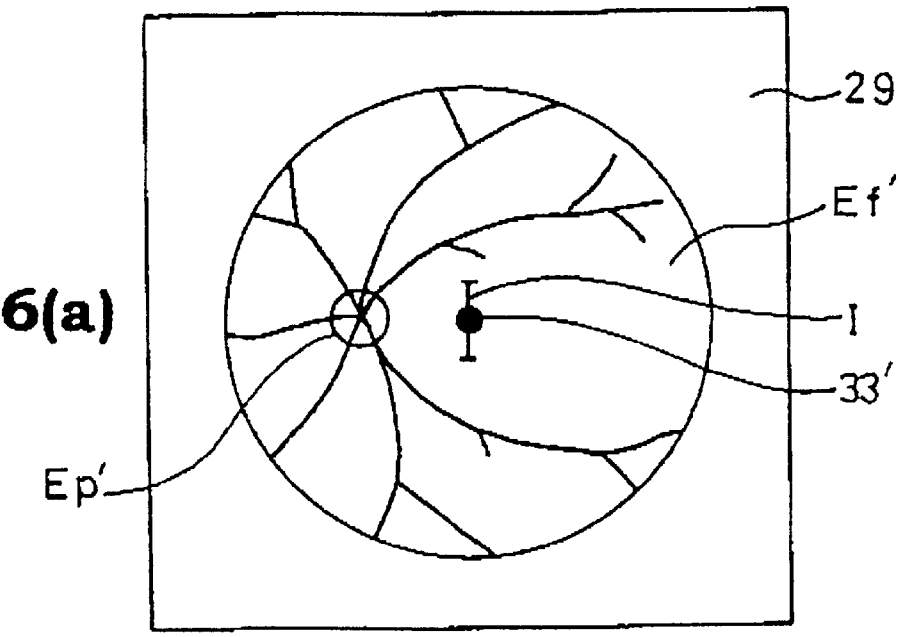

As shown in FIG. 6(a), a scale I for measuring the opening state of the pupil is displayed at the central position of the screen of the television monitor 29. The scale I is used also as an alignment index image reference position mark, i.e., a mark indicating a reference position at which the alignment index images 33' must be formed after the completion of alignment.

Operations of the fundus camera in the first embodiment for central part photographing and those for peripheral part photographing will be described in the following.

Operations for Central Part Photographing

When photographing a central part of the fundus Ef, a fixation mark selector switch, not shown, is operated to select and turn on the fixation light source 37 for central part photographing to align the visual line of the eye E with the optical axis $O_1$. Then, the inspector operates a joystick or the like to move the main unit for XY alignment and working distance adjustment. Operations for the XY alignment and the working distance adjustment will be inclusively called an alignment operation.

After the completion of the alignment operation, intermediate images of the alignment index images 33' are on the optical axis $O_1$ and on the plane R optically conjugate with the film 31, as shown in FIG. 3(a). On the television monitor 29, the focused alignment index images 33' is formed in coincidence with the scale I and observed with a focused state as shown in FIG. 5(a).

If the alignment operation is not completed, the defocused alignment index images 33' are displayed separately as shown in FIG. 5(b). The inspector operates the joystick or the like to move the main unit toward or away from the eye E to adjust the distance between the main unit and the eye E to the proper working distance W so that alignment index images 33' coincide with each other as shown in FIG. 5(a). If the alignment index images 33' displayed on the screen of the television monitor 29 do not coincide with the scale I, the main unit is moved up-and-down and left-and-right direction for XY alignment.

After the alignment operation is completed, the photographing button is pushed to obtain a photograph of the fundus image Ef'.

Operations for Peripheral Part Photographing

Figure 6B:
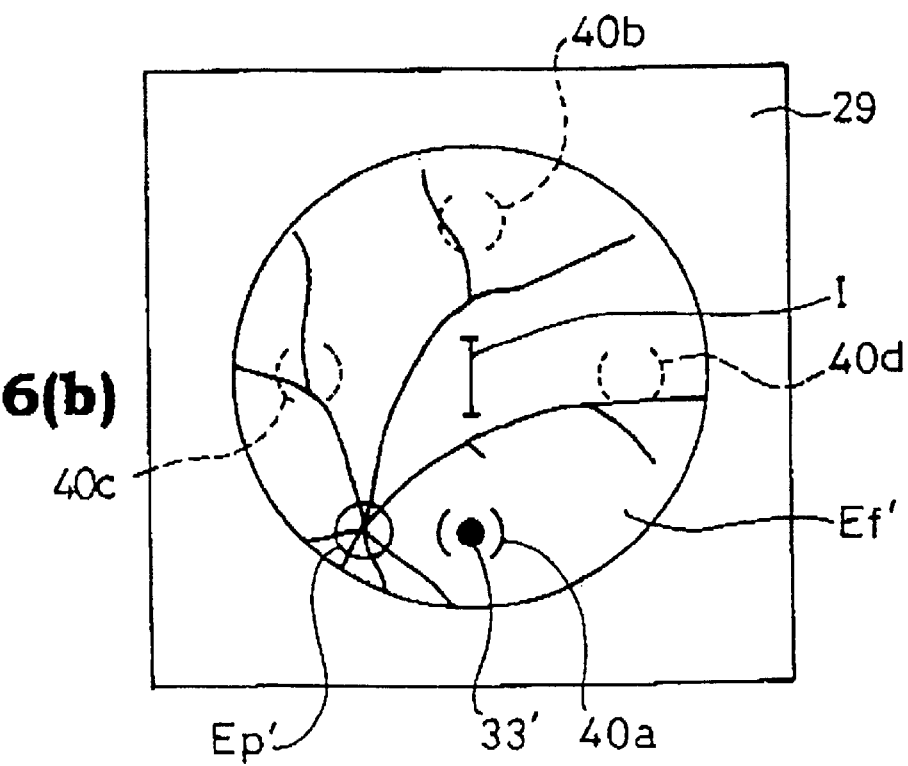

Now we will describe the peripheral part photographing. There is provided an example where an upper peripheral part of the fundus Ef of the eye E is photographed, namely the fundus image Ef' in which the optic papilla of the eye E is located in the lower half of the screen of the television monitor 29 is photographed. In this case, the fixation index selector switch, not shown, is operated to select and turn on the fixation light source 37 for directing the visual line of the subject's eye E upward. When the visual line has been directed upward by the fixation mark and the alignment operation has been completed, an image Ep' of the optical papilla is displayed in a lower half of the screen of the television monitor 29 as shown in FIG. 6(b).

When the fixation light source 37 for directing the visual line upward is turned on, an alignment reference position mark 40a is displayed in a lower part of the screen of the television monitor 29. The alignment reference position mark 40a indicates a position where the alignment index images 33' must be located when photographing an upper part of the fundus Ef.

Furthermore, in the fundus camera in the first embodiment, the light guide 33 is moved toward the eye E by a predetermined distance δ simultaneously with an operation for turning on the fixation light source 37 so that the proper working distance W' for photographing a peripheral part of the fundus Ef is greater than the proper working distance W for photographing a central part of the fundus Ef.

Figure 7:
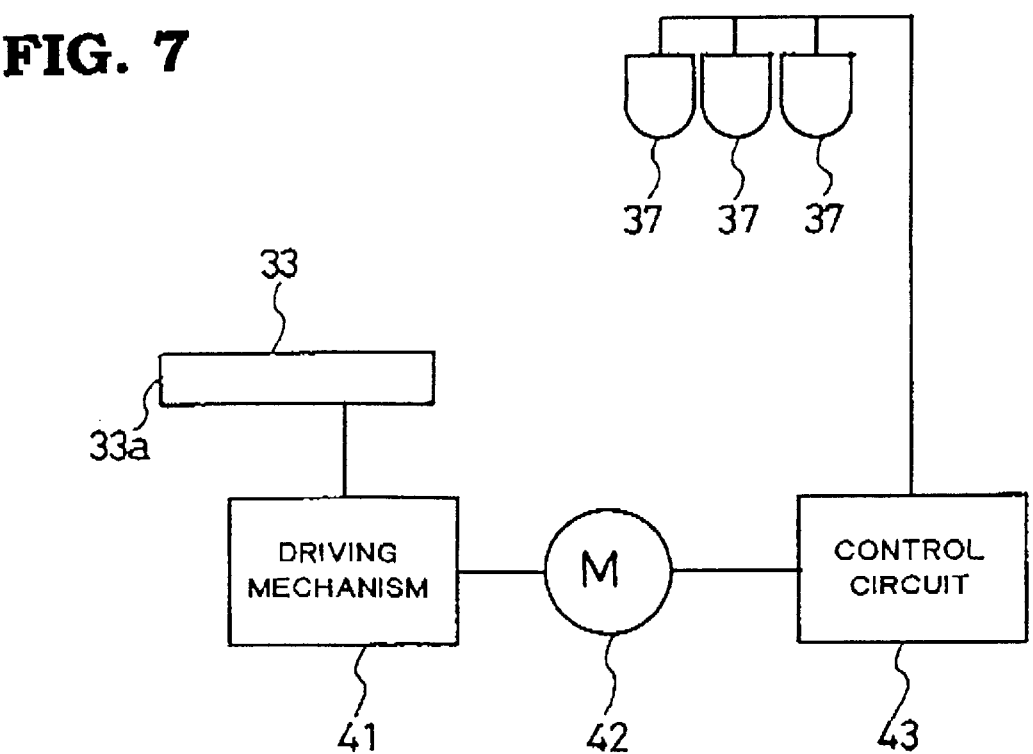
FIG. 7 is a block diagram of a light guide moving mechanism included in the first embodiment shown in FIG. 1.

Referring to FIG. 7, a light guide 33 is connected to a driving mechanism 41 driven by a pulse motor 42, the pulse motor 42 is connected to a control circuit 43, and the fixation light sources 37 and the fixation index selector switch (not shown), are connected to the control circuit 43. Upon the selection of the fixation light source 37 for photographing a peripheral part of the fundus Ef by operating the fixation index selector switch, the control circuit 43 turns on the selected fixation light source 37 and drives the pulse motor 42 for turning by predetermined degrees of rotation. Consequently, the light guide 33 is shifted by the distance δ along its optical axis, the exit end 33a is dislocated from a position conjugate with the relay lens 36 along the optical axis $O_1$ accordingly, and the position where the alignment image of the eye E is formed by the objective 19 is shifted away from the objective 19. Thus, the driving mechanism 41 and the pulse motor 42 constitute working distance changing means for shifting the alignment image of the eye E away from the objective 19 along the optical axis $O_1$ to increase the proper working distance. The driving mechanism 41 is a known mechanism capable of converting a rotating motion of the pulse motor 42 into a linear sliding motion of the light guide 33, such as a rack-and-pinion mechanism.

Figure 8:
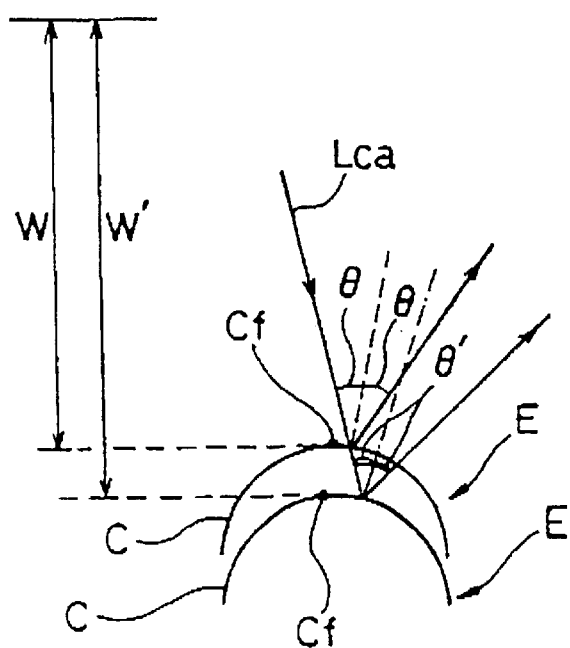
FIG. 8 is a diagrammatic view of assistance in explaining the change of the angle of the light reflected on the cornea, depending on the change of the proper working distance.

Referring to FIG. 8, when the proper working distance W is increased to the proper working distance W', a light beam Lca passing an edge of the cornea diaphragm 14 falls on a part of the cornea C at a distance from the corneal vertex Cf longer than the distance of a point on which the same light beam Lca falls from the vertex Cf when the proper working distance is W. Consequently, the angle θ' of reflection of the light beam Lca on the cornea C when the proper working distance is W' is greater than that when the proper working distance is W. Accordingly, the reflected light beam reflected from the cornea can be intercepted by a frame holding the objective 19 and the aperture mirror 18, does not enter the photographing optical system 7 and does not reach the camera tube 28 and the film 31 when the proper working distance W' for photographing a peripheral part of the fundus Ef is determined properly.

The proper working distance W' is greatly dependent on the optical design of the illuminating optical system 6 and the photographing optical system 7. In the fundus camera in this embodiment that illuminates the fundus Ef by the annular-slit illuminating light reflected by the aperture mirror 18, the increment ΔW=W'−W in the proper working distance is expected to be on the order of 1 mm. Since an excessively great increment ΔW affects the picture quality of the photograph, it is preferable to limit the distance δ to the least value necessary for preventing the entrance of the reflected light reflected from the cornea into the photographing optical system 7.

When the fixation light source 37 is turned on and the visual line of the eye E is directed upward, the alignment index images 33' are formed at positions shifted upward from the optical axis $O_1$ of the photographing optical system 7 as shown in FIG. 3(b) and at a position on the screen of the television monitor 29 coinciding with the alignment reference position mark 40a as shown in FIG. 6(b) in a state after the completion of alignment. Therefore, the inspector is able to complete an aligning operation by adjusting the position of the main unit so that the alignment images 33' coincide with the alignment reference position mark 40a.

Similarly, alignment reference marks 40b, 40c and 40d are displayed on the screen of the television monitor 29 when photographing a lower part, a right part and a left part, respectively, of the fundus Ef. The inspector is able to complete the operation for alignment by making the alignment index images 33' coincide with the alignment reference position mark 40b, 40c or 40d. In this embodiment, the position of the alignment reference position mark changes according to the position of the alignment index images 33' on the screen dependent on a part of the fundus Ef to be photographed. Therefore, the optical axis $O_1$ of the photographing optical system 7 can be easily aligned with the center of the subject's pupil.

Also when photographing any peripheral part of the fundus Ef, the light guide 33 is moved automatically toward the eye E by the predetermined distance δ so that the proper working distance W' is greater than the proper working distance W for photographing a central part of the fundus Ef. Therefore, the light emitted by the illuminating optical system 6 and reflected from the cornea does not enter the photographing optical system 7, the deterioration of the picture quality of photographs by detrimental light can be prevented and picture quality can be improved.

The fundus camera in this embodiment selects and displays the alignment reference position marks 40a, 40b, 40c or 40d according to the operation of the fixation mark selector switch, not shown. The fundus camera may be provided with photographing part selector switches respectively for selecting a central part, an upper part, a lower part, a right part and a left part, and, when one of the photographing part selector switches is operated, the corresponding one of the alignment reference position marks 40a, 40b, 40c and 40d may be displayed. Alternatively, it is possible that the operations of these switches are not associated with the displaying of the alignment reference position marks, the fundus camera may be provided with alignment reference position mark selector switches respectively for displaying the alignment reference position marks 40a, 40b, 40c and 40d, and the desired one of the alignment reference position marks 40a, 40b, 40c and 40d may be displayed by operating the corresponding alignment reference position mark selector switch.

Although the light guide 33 is moved automatically when the fixation light source 37 for photographing a peripheral part of the fundus Ef is turned on in the above embodiment, the light guide 33 may be manually moved by operating a micrometer head or the like. Further, the proper working distance may be changed by disposing a compensating lens or a plane parallel plate near the exit end 33a of the light guide 33 instead of moving the light guide 33 along its optical axis.

Figure 4B:
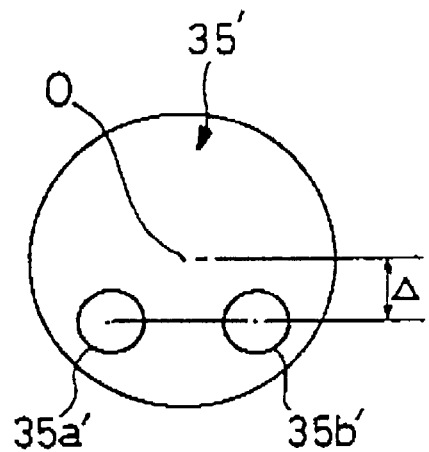
FIG. 4(b) is a front elevation of a two-hole diaphragm in a modification of the two-hole diaphragm shown in FIG. 4(a)

When photographing a peripheral part of the fundus Ef, the two-aperture diaphragm 35 may be replaced with a two-aperture diaphragm 35' shown in FIG. 4(b). The two-aperture diaphragm 35' is provided with apertures 35a' and 35b' on a line at a distance Δ from its center to prevent cutoff of the alignment light by the diaphragm and to facilitate alignment adjustment.

Second Embodiment

Figure 9A:
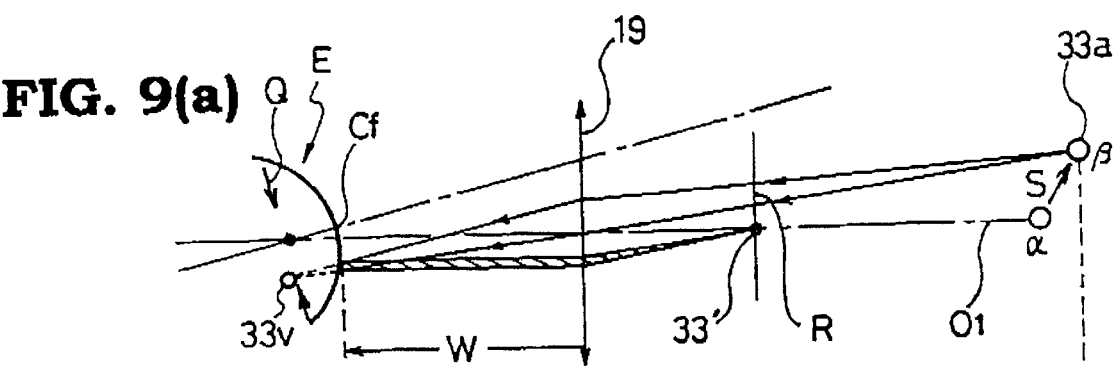
Figure 9B:
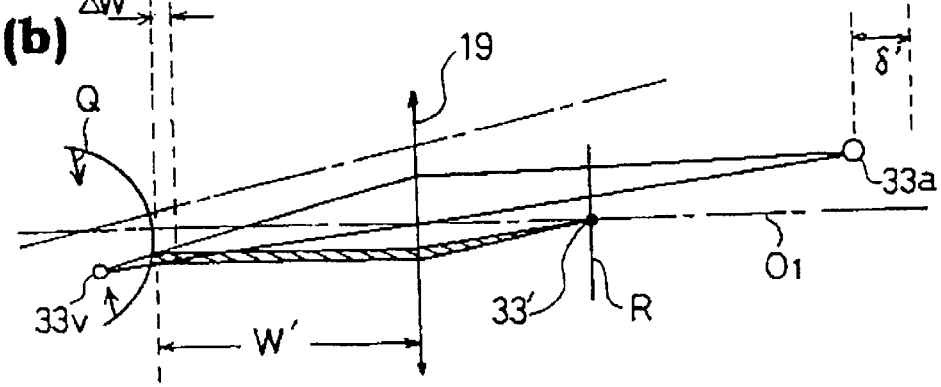

FIGS. 9(a) and 9(b) are diagrammatic views of assistance in explaining the principle of projecting an alignment index by a fundus camera in a second embodiment according to the present invention. The second embodiment differs from the first embodiment in that the exit end 33a of a light guide 33 is moved not only along its optical axis but also in the direction perpendicular to the optical axis by a plurality of pulse motors 42 and a driving mechanism 41. A control circuit 43 moves the exit end 33a in up-and-down and left-and-right directions so that the reference positions of alignment index images 33' coincide with a scale I displayed at the center of the screen of a television monitor 29 when photographing a peripheral part of the fundus. Therefore, a change of display for different alignment reference marks 40 is unnecessary. The second embodiment is the same in other respects as the first embodiment and hence further description thereof will be omitted.

The applicant of the present invention has proposed an invention similar to the second embodiment in Japanese Patent Application No. Hei 10-106115. As shown in FIG. 9(*a*), when photographing a peripheral part of the fundus by the invention disclosed in that patent application, the exit end 33*a* is shifted from a position α for photographing a central part of the fundus to a position β obliquely behind the position α as viewed from the eye E (i.e. along the arrow S) to form a virtual image 33*v* at a predetermined position on an end of a cornea focal plane Q inclined to an optical axis $O_1$. The position β is such that light rays which are reflected on the cornea C as if they are projected from its virtual image 33*v* become parallel and the image of the exit end 33A is formed on the fundus conjugate plate R and on the optical axis $O_1$ when alignment is completed. When the exit end 33*a* is shifted to the position β in case of peripheral part photographing, the alignment index images 33' coincide with the scale I and the same proper working distance W is used for both the cases of photographing a central part of the fundus and photographing a peripheral part of the fundus.

However, as mentioned above, in the case where the same proper working distance W is used for both the cases of photographing a central part of the fundus and photographing a peripheral part of the fundus, reflected light from the cornea enters the photographing optical system 7 to deteriorate the picture quality of the photograph of the fundus. In the second embodiment, the exit end 33*a* of the light guide 33 is shifted from the position β toward the eye E by a distance δ' as shown in FIG. 9(*b*) when photographing a peripheral part of the fundus to use a proper working distance W' longer than the proper working distance W for photographing a central part of the fundus. The distance δ' is dependent on the design of the optical system.

In the second embodiment, the proper working distance may be changed by any suitable means other than shifting the light guide 33. For example, a wedge prism may be disposed near the exit end 33*a* or a compensating lens may be inserted in the optical system with its optical axis deviating from the optical axis of the optical system.

Third Embodiment

When photographing a peripheral part of the fundus by the fundus camera in each of the two foregoing embodiments, the proper working distance longer than that for photographing a central part of the fundus is used to prevent the adverse effect of detrimental light on photographs. The third embodiment uses the same proper working distances for both the cases of photographing a central part of the fundus and photographing a peripheral part of the fundus. Instead, a plurality of cornea diaphragms differing from each other in shape or size are provided, and when photographing a peripheral part of the fundus a cornea diaphragm 14 is replaced.

Figure 10A:
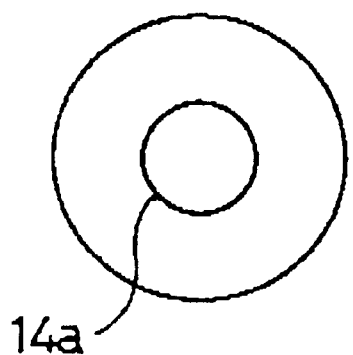
Figure 10B:
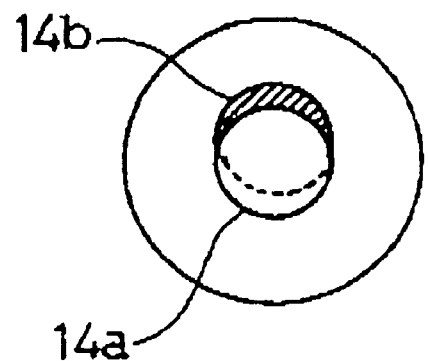

For example, two cornea diaphragms, namely, a cornea diaphragm 14*a* having its center coinciding with the optical axis $O_1$ and a cornea diaphragm 14*b* having its center not coinciding with the optical axis $O_1$, are prepared. Only the cornea diaphragm 14*a* is inserted in the optical path as shown in FIG. 10(*a*) when photographing a central part of the fundus, and both the cornea diaphragms 14*a* and 14*b* are inserted in the optical path as shown in FIG. 10(*b*) when photographing a peripheral part of the fundus. Thus, a light shading area when photographing a peripheral part of the fundus is greater by a shaded area shown in FIG. 10(*b*) than that when photographing a central part of the fundus, so that the entrance of the light reflected on the cornea into the photographing optical system 7 can be prevented. The position of the shaded area around the optical axis is dependent on the arrangement of the parts of the optical system. In the optical system shown in FIG. 1, it is preferable that the shaded area be displaced in a direction opposite a direction in which the optical axis of the eye E inclines.

Figure 11A:
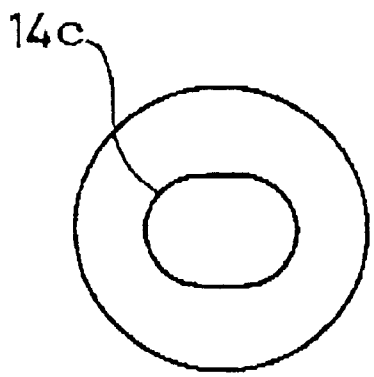
Figure 11B:
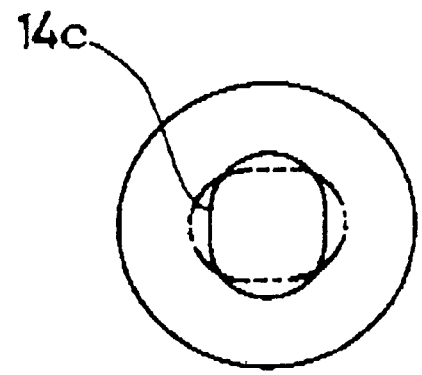
Figure 12A:
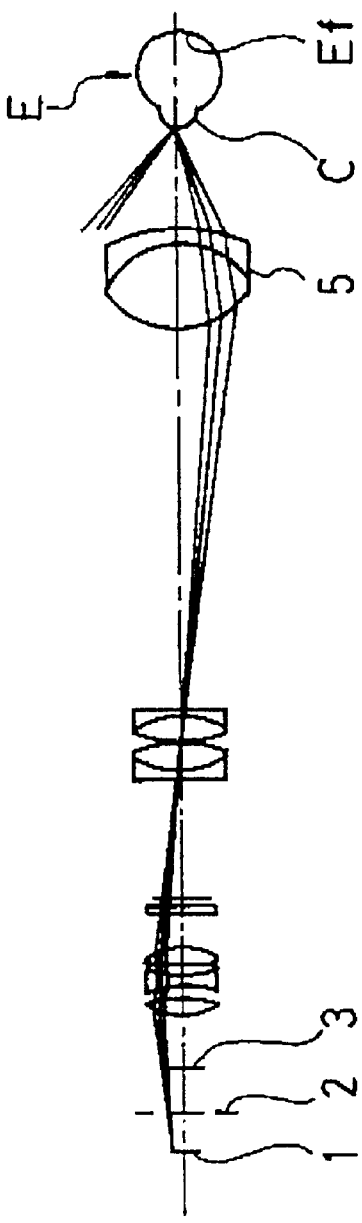
Figure 12B:
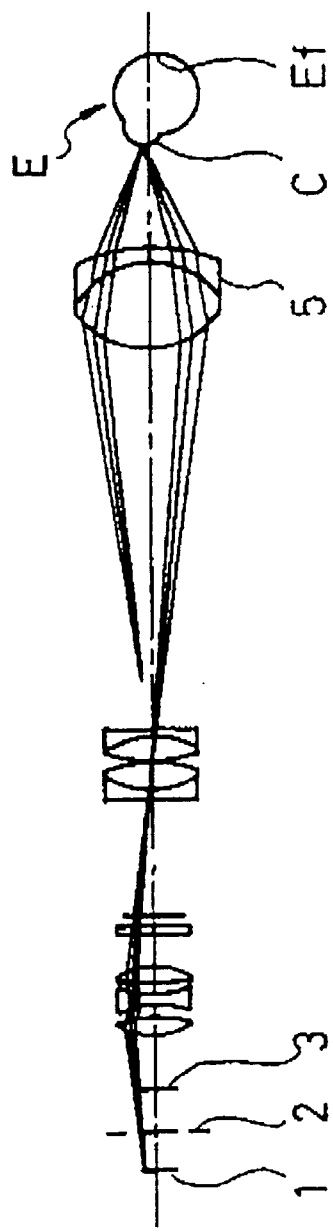

A cornea diaphragm 14*c* having an elongate shading part shown in FIGS. 11(*a*) and 11(*b*) may be used. The cornea diaphragm 14*c* is held so as to be turnable about its optical axis, the cornea diaphragm 14*c* is set in a state as shown in FIG. 11(*a*) for photographing a central part, a right part or a left part of the fundus and is turned through an angle of 90° from the position shown in FIG. 11(*a*) to set the same in a state as shown in FIG. 11(*b*) when photographing an upper part or a lower part of the fundus.

Although the invention has been described in its preferred form with a certain degree of particularity, obviously many changes and variations are possible therein. It is therefore to be understood that the present invention may be practiced otherwise than as specifically described herein without departing from the scope and spirit thereof.

What is claimed is:

1. A fundus camera comprising:
    a main unit equipped with an illuminating system for illuminating a fundus of an eye to be inspected and a photographing system for photographing the fundus;
    a working distance detecting means for detecting whether a distance between the eye and the main unit is equal to a proper working distance or not; and
    a working distance changing means for changing the proper working distance depending on whether photographed part is a central part of the fundus or a peripheral part of the fundus.

2. The fundus camera according to claim 1, further comprising a fixation mark projecting system for projecting a fixation mark to guide a visual line of the eye at a position corresponding to a part to be photographed when photographing the peripheral part of the fundus, wherein the working distance changing means changes the proper working distance according to change of the position where the fixation mark is projected.

3. The fundus camera according to claim 1, wherein the working distance detecting means projects alignment index on the eye and detects whether a proper working distance is secured on the basis of a reflected light, and the working distance changing means changes the proper working distance by shifting a position of the index the along an optical axis of the photographing optical system.

4. The fundus camera according to claim 3, further comprising a fixation mark projecting system for projecting a fixation mark to guide a visual line of the eye at a position corresponding to a part to be photographed when photographing the peripheral part of the fundus, wherein the working distance changing means changes the proper working distance according to change of the position where the fixation mark is projected.

* * * * *